Figure 1:
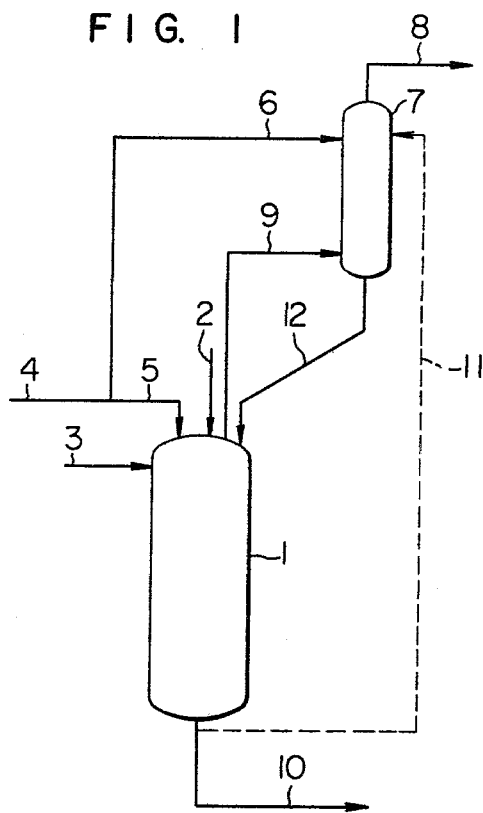

United States Patent [19]

Matsumoto et al.

[11] 4,319,044

[45] Mar. 9, 1982

[54] PROCESS FOR RECOVERING USEFUL COMPONENTS FROM WASTE GAS OF METHIONINE SYNTHESIS

[75] Inventors: Genya Matsumoto; Munetaka Sakai; Shigeki Nakata; Toshio Kawabata, all of Niihama, Japan

[73] Assignee: Sumitomo Chemical Company, Limited, Osaka, Japan

[21] Appl. No.: 113,316

[22] Filed: Jan. 18, 1980

[30] Foreign Application Priority Data

Jan. 25, 1979 [JP] Japan .................................. 54-7852

[51] Int. Cl.$^3$ ........................................ C07C 149/247
[52] U.S. Cl. .................................................. 562/559
[58] Field of Search .............................. 562/559, 575

[56] References Cited

FOREIGN PATENT DOCUMENTS 745432  7/1970 Belgium ............................. 562/559
2149185  3/1973 France ................................ 562/559
38-14715 8/1963 Japan .................................. 562/559
43-29929 12/1968 Japan .................................. 562/575

*Primary Examiner*—Michael L. Shippen
*Attorney, Agent, or Firm*—Stevens, Davis, Miller & Mosher

[57] ABSTRACT

In the methionine synthesis involving a hydantoin reaction in its steps, a process for recovering and reusing the useful components in the waste gas by (1) washing the waste gas generated in the hydantoin synthesis reactor with methylmercaptopropionaldehyde (hereinafter referred to as MA) and returning the washing into the MA synthesis reactor system and/or (2) washing the waste gas with an aqueous solution of a compound substantially constituted of ammonia and carbon dioxide, i.e. the starting material of hydantoin synthesis, or with the liquid reaction mixture of methionine containing hydantoin (hereinafter referred to as MH) and returning the washing into the MH synthesis reactor system.

7 Claims, 2 Drawing Figures

PROCESS FOR RECOVERING USEFUL COMPONENTS FROM WASTE GAS OF METHIONINE SYNTHESIS

This invention relates to a process for recovering and reusing useful components in the waste gas which is generated in the hydantoin synthesis reactor in the methionine synthesis involving a hydantoin reaction in its steps.

As the synthetic process of hydantoin (hereinafter referred to as MH) in the above-mentioned methionine production, there are known a process which comprises synthesizing MH from methylmercaptopropionaldehyde (hereinafter referred to as MA), obtainable by reacting methyl mercaptan (hereinafter referred to as MM) with acrolein in the presence of an appropriate catalyst, hydrogen cyanide and a compound substantially constituted of ammonia and carbon dioxide (hereinafter referred to as AC) such as ammonium carbonate, ammonium bicarbonate and the like as starting materials, and a process which comprises synthesizing MH in one step in the presence of an appropriate catalyst by using MM, acrolein, hydrogen cyanide and AC such as ammonium carbonate, ammonium bicarbonate or the like as starting materials. In either of these reactions, the hydrogen cyanide is usually added in excess (by mole) to MA, acrolein or MM for the purpose of completing the reaction.

Though the excess hydrogen cyanide partially dissolves into the MH solution, its major part is liberated as gaseous hydrogen cyanide.

As a process for treating this gaseous hydrogen cyanide, there have hitherto been proposed the oxidative decomposition process using an oxidant such as chlorine, hypochlorite or the like, the catalytic hydrolysis process using an alkali metal hydroxide supported on a carrier such as alumina, silica or the like (Japanese Patent Kokai (Laid-Open) No. 59074/1974), etc. When the gas generated in the MH synthesis reactor is directly treated, however, any of these processes requires a large quantity of oxidant or catalyst. Since hydrogen cyanide is expensive, these processes by which hydrogen cyanide is not recovered but decomposed cannot be economical industrially. Further, according to the former process among the above-mentioned MH syntheses, the main starting material MA is usually synthesized from MM and acrolein as expressed by the reaction scheme shown below:

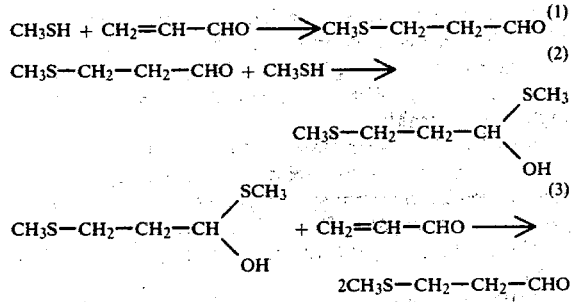

$$CH_3SH + CH_2=CH-CHO \longrightarrow CH_3S-CH_2-CH_2-CHO \quad (1)$$

$$CH_3S-CH_2-CH_2-CHO + CH_3SH \longrightarrow CH_3S-CH_2-CH_2-CH\begin{matrix}SCH_3\\ \\OH\end{matrix} \quad (2)$$

$$CH_3S-CH_2-CH_2-CH\begin{matrix}SCH_3\\ \\OH\end{matrix} + CH_2=CH-CHO \longrightarrow 2CH_3S-CH_2-CH_2-CHO \quad (3)$$

In this case, the intermediate hemithioacetal partially remains in MA. If it is fed into the MH synthesis reactor, it decomposes to liberate an equimolar quantity of MM. Furthermore, if MA decomposes in the reactor, MM is still formed there. In the latter process, the unreacted MM is discharged as it is into the waste gas. Accordingly, the waste gas discharged from the hydantoin reactor contains MM in addition to hydrogen cyanide.

As a process for treating this MM, there have hitherto been proposed the oxidative decomposition process using an oxidant such as chlorine, hypochlorite or the like, the process which comprises oxidatively treating it with a mixture of iron salt, amine and acetate (Japanese Patent Kokai (Laid-Open) No. 117690/1975), etc. When the gas generated in the MH synthesis reactor is directly treated, however, any of these processes requires a large quantity of oxidant. In addition, since MM is expensive, these processes by which MM is not recovered but decomposed cannot be economical industrially.

In view of above, the present inventors conducted extensive studies to find out that hydrogen cyanide can be absorbed selectively and stably by an aqueous solution of AC or by MH-containing liquid reaction mixture, which are both starting materials for the synthesis of MH similarly to hydrogen cyanide, and thereby hydrogen cyanide can be recovered and reused and that MM can effectively be recovered and reused by a counter-current contact of MA and MM-containing waste gas. Based on these findings, this invention was accomplished.

It is the object of this invention to provide a process for recovering and reusing the hydrogen cyanide or MM in the waste gas generated in the hydantoin synthesis reactor in the methionine synthesis involving a hydantoin reaction in its steps.

In the methionine synthesis involving a hydantoin reaction in its steps, this invention provides a process for recovering the useful components from the waste gas of methionine synthesis which comprises washing the waste gas generated in the hydantoin synthesis reactor with MA and returning the washing to the MA synthesis reactor and/or washing the waste gas with an aqueous solution of AC which is a starting material of hydantoin synthesis or with a hydantoin-containing liquid reaction mixture of methionine and returning the washing to the hydantoin synthesis reactor.

According to the process of this invention, hydrogen cyanide or MM can be recovered into the system effectively, so that the consumption of MM and hydrogen cyanide can be decreased to a great extent and the agent for making them harmless can be economized to a great extent. Therefore, the process of this invention is very advantageous over the prior processes from the industrial point of view.

An example of the embodiment of this invention will be illustrated with reference to the drawings.

Figure 2:
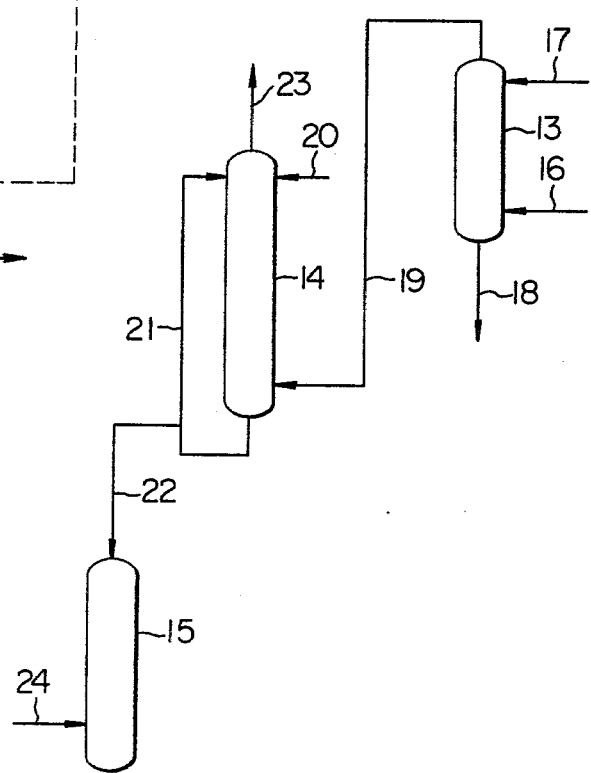

FIG. 1 and FIG. 2 are sheets illustrating one embodiment of the process for recovering and reusing hydrogen cyanide and MM, respectively.

In FIG. 1, hydrogen cyanide is fed into MH synthesis reactor 1 through piping 2, an aqueous solution of AC is fed thereinto through pipings 4 and 5, and MA (or acrolein and MM) and catalyst are fed thereinto through piping 3. Usually, this reaction is carried out at a temperature of 30°–100° C. and at a pressure of 1 kg/cm² G or less.

The gas generated in this reactor 1 is mainly constituted of carbon dioxide, hydrogen cyanide and MM. It is sent to the absorbing tower 7 through piping 9. In this tower, it is "counter-current"-wise contacted with an aqueous solution of AC or with a MH-containing liquid reaction mixture, whereby the major portion of the hydrogen cyanide is absorbed off. The aqueous solution of AC is supplied to the absorbing tower through piping 6, while the MH-containing liquid reaction mixture is supplied there through piping 11. In any case, the absorbing fluid returns to reactor 1 through piping 12.

As shown in the drawing, a portion of the aqueous solution of AC employed as a starting material of MH synthesis may be used as an absorber. Otherwise, its whole quantity added to the continuous process system may be used as an absorber.

The recovery of MM is carried out, for example, in such a manner as shown in FIG. 2. The gas generated in the MH synthesis reactor is sent to the water-washing tower 13 through piping 16. In this tower, it is "counter-current"-wise contacted with the water introduced through piping 17 and from the top of the tower, whereby the small quantity of ammonia is absorbed off. The gas generated in MH synthesis reactor contains MM, hydrogen cyanide and ammonia. Though MA is usually instable in the presence of ammonia and changes into a high-boiling material such as polymer, the water-washing tower 13 may be omitted when the quantity of the ammonia is very small or when the residence time of MA in the MM absorbing tower 14 of the subsequent step is so short that absorption of a slight quantity of ammonia makes no significant trouble. The gas mainly comprising MM is sent through piping 19 into MM absorbing tower 14, where it is "counter-current"-wise contacted with the MA which enters the tower from the top through piping 20, whereby the major part of the MM is absorbed off. The water-washing tower 13 and the absorbing tower 14 are preferably operated under a pressure of 0-2 kg/cm² G and at a temperature of 0°-50° C.

Since this absorption is a chemical absorption as has been mentioned before, it is also possible to recycle and resuse the MA containing the chemically absorbed MM, as shown in the drawing, and an apparatus for prolonging the residence time may be attached to the still part of the absorbing tower or to the cycle line for the purpose of making the progress of reaction more sufficient. It is also possible to attach an adequate cooling device for the purpose of removing the heat of condensation of steam in the gas or removing the heat of reaction.

The MM absorbed in MA passes piping 22 and enters MA reactor 15, where it reacts with the acrolein flowing thereinto through piping 24 in the presence of an appropriate catalyst to give MA.

On the other hand, the gas from which MM has been removed flows out from piping 23. Since its main component is carbon dioxide, it can be effectively utilized for other objects such as reuse as a starting material for the synthesis of AC.

Further, in the latter embodiment, i.e. in the case where MH is synthesized in one step without previously synthesizing MA, it is of course possible to wash the waste gas of MH synthesis reactor containing hydrogen cyanide and MM first with an aqueous solution of AC or the hydantoin-containing liquid reaction mixture, return the washing into the MH synthesis reactor, then wash the waste gas from which hydrogen cyanide has been removed with MA in order to remove MM from the waste gas, and return the MA containing the absorbed MM into the MA synthesis reactor. This process is desirable in that both MM and hydrogen cyanide can be recovered and reused.

This invention will be illustrated with reference to the following examples. This invention is not limited by these examples.

EXAMPLE 1

MH synthesis was carried out by continuously adding hydrogen cyanide and aqueous solution of ammonium bicarbonate to MA, wherein the proportions of hydrogen cyanide and $NH_4HCO_3$ to MA were 1.2:1 and 3:1, respectively, by mole. The waste gas generated had a composition of: 4% by volume of hydrogen cyanide, 2.6% by volume of methyl mercaptan and 93.4% by volume of carbon dioxide.

30 Nl/hr of this waste gas was continuously contacted "counter-current"-wise in an absorbing tower at a temperature of 30° C., under the atmospheric pressure and at a liquid-gas ratio (weight of 13% by weight aqueous solution of ammonium bicarbonate/weight of waste gas) of 10. The gas obtained contained 100 ppm of hydrogen cyanide and 2.5% by volume of methyl mercaptan, and the remainder was substantially carbon dioxide.

MH synthesis was again carried out by using the aqueous solution of ammonium bicarbonate which has absorbed hydrogen cyanide in the absorbing tower in the above-mentioned manner, hydrogen cyanide from which the quantity of hydrogen cyanide absorbed in the absorbing tower has been deducted, an aqueous solution of ammonium bicarbonate from which the quantity of aqueous solution of ammonium bicarbonate used for the absorption has been deducted, and MA. The liquid reaction mixture of the first synthesis and the liquid reaction mixture of the latter synthesis using the absorbing solution were separately hydrolyzed with caustic soda and neutralized with sulfuric acid. The yield of methionine thus obtained was 90% in both cases.

EXAMPLE 2

The same waste gas as in Example 1 was "counter-current"-wise contacted with a liquid reaction mixture containing 10% by weight of MH at a temperature of 40° C. under the atmospheric pressure and at a liquid-gas ratio of 10. The gas obtained contained 200 ppm of hydrogen cyanide and 2.6% by volume of methyl mercaptan.

EXAMPLE 3

1 Nm³/hr of waste gas generated from MH synthesis reactor, containing 100 ppm of hydrogen cyanide, 2.5% by volume of MM and the residual quantity of carbon dioxide, was directly contacted "counter-current"-wise with water in a water-washing tower at a temperature of 20° C., under the atmospheric pressure and at a liquid-gas ratio (by weight) of 3. The gas obtained contained 2.4% by volume of MM and a trace quantity of hydrogen cyanide.

In MM absorbing tower, this gas was contacted "counter-current"-wise with MA at a temperature of 15° C., under the atmospheric pressure and at a liquid-gas ratio (by weight) of 0.7. The concentration of MM in the gas discharged from the absorbing tower was 100 ppm.

0.4% by weight of a catalyst (25% by weight of pyridine, 75% by weight of acetic acid) was added to the MM-containing MA solution obtained by this process and thoroughly mixed, after which acrolein was added in an equimolar amount to the absorbed MM while keeping the temperature at 40° C. The colorless transparent liquid thus obtained was analyzed by gas chromatography to reveal that the increase in the quantity of MA corresponded to a yield of 97% based on the acrolein added.

EXAMPLE 4

The procedure of Example 3 was repeated, except that, in the continuous treatment, the counter-current contact of waste gas and MA was carried out at 20° C., under the atmospheric pressure and at a liquid-gas ratio of 4, the amount of fresh MA supplied was 1/20 of the recycled MA, and the residence time of MA was 30 hours. Thus, the concentration of MM in the outlet gas was 400 ppm.

An experiment of the same MA synthesis as in Example 3 was carried out by using this MM-absorbing solution. The yield of MA was 96.5% based on the acrolein added.

What is claimed is:

1. In a process for the production of methionine comprising the steps of reacting (1) methylmercaptopropionaldehyde or a combination of methyl mercaptan and acrolein, (2) hydrogen cyanide and (3) a compound selected from the group consisting essentially of ammonium carbonate and ammonium bicarbonate in a hydantoin synthesis reactor system to form a hydantoin and a waste gas, and hydrolyzing said hydantoin to form methionine, the improvement comprising recovering hydrogen cyanide by washing said waste gas generated in the hydantoin synthesis reactor, containing methyl mercaptan and hydrogen cyanide, with an aqueous solution of a compound selected from the group consisting essentially of ammonium carbonate and ammonium bicarbonate, which is the starting material of hydantoin synthesis and returning the washing to the hydantoin synthesis reactor system.

2. In a process for the production of methionine comprising the steps of reacting (1) methylmercaptopropionaldehyde or a combination of methyl mercaptan and acrolein, (2) hydrogen cyanide and (3) a compound selected from the group consisting essentially of ammonium carbonate and ammonium bicarbonate in a hydantoin synthesis reactor system to form a hydantoin and a waste gas, and hydrolyzing said hydantoin to form methionine, the improvement comprising recovering hydrogen cyanide by washing said waste gas generated in the hydantoin synthesis reactor, containing methyl mercaptan and hydrogen cyanide, with hydantoin-containing liquid reaction mixture from the hydantoin synthesis reactor and returning the washing to the hydantoin synthesis reactor system.

3. In a process for the production of methionine comprising the steps of reacting methyl mercaptan and acrolein in a methylmercaptopropionaldehyde synthesis reactor system to form methylmercaptopropionaldehyde, reacting (1) said methylmercaptopropionaldehyde, (2) hydrogen cyanide and (3) a compound selected from the group consisting essentially of ammonium carbonate and ammonium bicarbonate in a hydantoin synthesis reactor system to form a hydantoin and a waste gas, and hydrolyzing said hydantoin to form methionine, the improvement comprising recovering methyl mercaptan by washing said waste gas generated in the hydantoin synthesis reactor, containing methyl mercaptan and hydrogen cyanide, with methylmercaptopropionaldehyde and returning the washing to the methylmercaptopropionaldehyde synthesis reactor system.

4. In a process for the production of methionine comprising the steps of reacting methyl mercaptan and acrolein in a methylmercaptopropionaldehyde synthesis reactor system to form methylmercaptopropionaldehyde, reacting (1) said methylmercaptopropionaldehyde, (2) hydrogen cyanide and (3) a compound selected from the group consisting essentially of ammonium carbonate and ammonium bicarbonate in a hydantoin synthesis reactor system to form a hydantoin and a waste gas, and hydrolyzing said hydantoin to form methionine, the improvement comprising recovering hydrogen cyanide by washing said waste gas generated in the hydantoin synthesis reactor, containing methyl mercaptan and hydrogen cyanide, with an aqueous solution of a compound selected from the group consisting essentially of ammonium carbonate and ammonium bicarbonate, which is the starting material of hydantoin synthesis and returning the washing to the hydantoin synthesis reactor system, and thereafter recovering methyl mercaptan by washing the waste gas thus treated with methylmercaptopropionaldehyde and returning the washing to the methylmercaptopropionaldehyde synthesis reactor system.

5. In a process for the production of methionine comprising the steps of reacting methyl mercaptan and acrolein in a methylmercaptopropionaldehyde synthesis reactor system to form methylmercaptopropionaldehyde, reacting (1) said methylmercaptopropionaldehyde, (2) hydrogen cyanide and (3) a compound selected from the group consisting essentially of ammonium carbonate and ammonium bicarbonate in a hydantoin synthesis reactor system to form a hydantoin and a waste gas, and hydrolyzing said hydantoin to form methionine, the improvement comprising recovering hydrogen cyanide by washing said waste gas generated in the hydantoin synthesis reactor, containing methyl mercaptan and hydrogen cyanide, with hydantoin-containing liquid reaction mixture from the hydantoin synthesis reactor and returning the washing to the hydantoin synthesis reactor system, and thereafter recovering methyl mercaptan by washing the waste gas thus treated with methylmercaptopropionaldehyde and returing the washing to the methylmercaptopropionaldehyde synthesis reactor system.

6. A process according to claim 3, 4 or 5, wherein the waste gas is rinsed with water prior to washing with methylmercaptopropionaldehyde.

7. A process according to claim 1, 2, 3, 4 or 5, wherein said aqueous solution of a compound selected from the group consisting essentially of ammonium carbonate and ammonium bicarbonate is an aqueous solution of ammonium bicarbonate.

* * * * *